US00PP22358P2

(12) United States Plant Patent
Finn

(10) Patent No.: US PP22,358 P2
(45) Date of Patent: Dec. 20, 2011

(54) BLACKBERRY PLANT NAMED 'ONYX'

(50) Latin Name: ***Rubus* hybrid**
Varietal Denomination: ONYX

(75) Inventor: Chad Elliott Finn, Corvallis, OR (US)

(73) Assignee: The United States of America as represented by the Secretary of Agriculture, Washington, DC (US)

( * ) Notice: Subject to any disclaimer, the term of this patent is extended or adjusted under 35 U.S.C. 154(b) by 0 days.

(21) Appl. No.: 12/660,189

(22) Filed: Feb. 22, 2010

(51) Int. Cl.
*A01H 5/00* (2006.01)

(52) U.S. Cl. ..... Plt./203

(58) Field of Classification Search ..... Plt./203
See application file for complete search history.

*Primary Examiner* — June Hwu

(74) *Attorney, Agent, or Firm* — John D. Fado; Gail E. Poulos

(57) ABSTRACT

Description and specifications of a new and distinct blackberry cultivar which originated from seed produced by a hand pollinated cross of OSC 1466 (non-patented)×ORUS 1117-11 (non-patented) is provided. This new trailing blackberry cultivar can be distinguished by its high yields, large fruit size, excellent fresh fruit quality, mid-late season fruit ripening, and healthy plants.

3 Drawing Sheets

Figure 1:
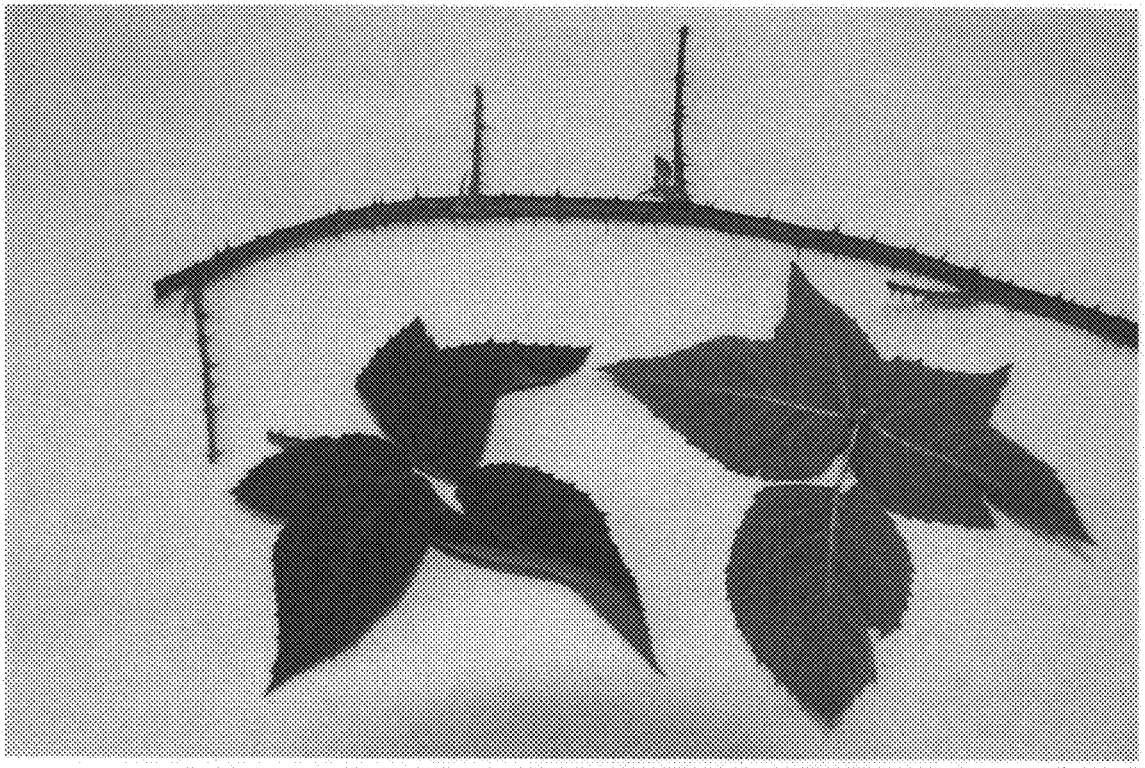

Latin name of the genus and species of the plant claimed: 'ONYX' is a new blackberry hybrid plant that is a *Rubus* subgenus *Rubus,* hybrid.

Variety denomination:

The new blackberry hybrid plant claimed is of the variety denominated 'ONYX', containing mostly *Rubus* subgenus *Rubus* germplasm.

BACKGROUND OF THE INVENTION

The present invention relates to the discovery of a new and distinct cultivar of blackberry hybrid plant botanically know as a *Rubus* subgenus *Rubus* hybrid and herein referred to as 'ONYX', as herein described and illustrated.

The new and distinct cultivar of blackberry originated from a hand pollinated cross of OSC 1466 (non-patented)×ORUS 1117-11 (non-patented).

Plants and fruit of this new cultivar differ phenotypically from its parents. The new cultivar is later ripening and larger in fruit size than the female parent OSC 1466 (non-patented) and has firmer, more uniformly shaped fruit than the male parent ORUS 1117-11 (non-patented). The new cultivar also has thorny canes, unlike the ORUS 1117-11 (non-patented) parent. The new cultivar has higher yields of firmer fruit than either of the parent blackberries. Although blackberries (*Rubus* subgenus *Rubus*) are highly heterogeneous and outcrossing, and most clones contain genes from more than one species, the new cultivar and its progenitor lines phenotypically exhibit characters predominately of the trailing western United States species, *Rubus ursinus* Cham et. Schltdl. (western trailing blackberry). *Rubus idaeus L.,* (red raspberry), *R. armeniacus* Focke (Himalaya blackberry). *R. baileyanus* Britton, and *R. argutus* Link Porter (highbush blackberry) can all be found in the pedigree of this new cultivar.

The seeds resulting from this controlled hybridization were germinated in a greenhouse in the winter of 1995 and planted in a field in Corvallis, Oreg. in the spring. The seedlings fruited during the summer of 1997 and one, designated ORUS 1523-4, was selected for its mid-late season ripening, large fruit size, excellent fruit quality, and excellent plant health.

During 1997, the original plant selection was propagated asexually from dormant, hardwood cane cuttings from the above noted location. An observational plot of 3 plants was established at the above noted location and at Aurora, Oreg. in the spring of 1998. Subsequently, larger replicated plantings were established Aurora, Oreg. with asexually multiplied plants.

The new cultivar has been asexually multiplied annually since 1997 by the use of cane cuttings. The new cultivar was established in vitro from a cane cutting and microcuttings have been taken and rooted from this sort of culture. During all asexual multiplication, the characteristics of the original plant have been maintained and no aberrant phenotypes have appeared.

Test plantings over a wide geographic area have shown this new cultivar to be adapted to differing soil and climatic conditions although it is best adapted to Mediterranean type climates where trailing blackberries are typically grown.

Plants of the new cultivar are vigorous and prolific and establish well after planting. Primocanes and floricanes have typical trailing blackberry growth habit. The plants are thorny with size and density of thorns being less than 'Marion' (non-patented) at the base, comparable at midpoint, and more thorny at the terminus. The primocanes emerge and grow vertically for 30-60 cm before arching to the ground and growing along the ground. Primocanes are typically lifted and tied onto a trellis system and after going through the dormant period break bud, flower and fruit as floricanes. Plants show no particular susceptibility to anthracnose [*Elsinoe veneta* (Burkh.) Jenkins], septoria (*Septoria rubi* Westend), cane blight (*Leptosphaeria coniothyrium* ([Fuckel] Sacc.) spur blight (*Didymella applanata* [Niessl] Sacc.), and purple blotch (*Septocyta ruborum* [Lib.] Petr.) nor have they tested positive for *Raspberry bushy dwarf* virus. The bloom period of the new cultivar averages 4-5 days later than the 'Marion' (non-patented) and 8-11 days later than 'Black Diamond' (non-patented).

Fruit of the new cultivar begin ripening 19 days later than 'Siskiyou' (non-patented) and 9 days later than 'Marion' (non-patented). The average harvest date of 5% ripe fruit is 9

July, of 50% ripe fruit is 16 July, and 1 August for 95% ripe fruit in the Willamette Valley of Oregon and the midpoint of harvest is 7 days later than for 'Marion' (non-patented). Fruit yields of the new cultivar are usually around 14, 309 kg/hectare (6.39 tons/acre) and are comparable to those for 'Marion' (non-patented). Yields are consistent from year to year.

The fruit is conical, with very uniformly sized, shaped and arranged drupelets giving the fruit a very uniform, attractive shape. The fruit are bright glossy black. The fruit is medium large (6.1 g) and typically 1 g larger than 'Marion' (non-patented) and 0.5 g smaller than 'Siskiyou' (non-patented). The new cultivar maintains a uniform fruit size throughout the harvest season. The new cultivar exhibits excellent fruit fertility with full drupelet set in contrast to 'Siskiyou' (non-patented), which can have poorly set fruit tips; it also has much better drupelet set than 'Marion' (non-patented). The fruit is firm at maturity, rating much higher than 'Marion' (non-patented) and comparable to 'Metolius' (non-patented) and 'Siskiyou' (non-patented).

The fresh fruit rates very good in flavor, being comparable to 'Obsidian' (non-patented), 'Metolius' (non-patented), and 'Kotata' (non-patented) but slightly lower than 'Marion' (non-patented) or 'Siskiyou' (non-patented). The flavor is sweet with a nice acidic balance with aroma typical of western blackberries. The fruit texture is comparable to 'Marion' (non-patented), 'Metolius' (non-patented), 'Obsidian' (non-patented), and 'Siskiyou' (non-patented) and the seeds are much less noticeable than in 'Chester Thornless' (non-patented) and 'Ouachita' (U.S. Plant Pat. No. 17,162). The soluble solids concentration averages 13.7% on shiny black fruit, similar to 'Marion' (non-patented) (13.3%) and lower than 'Navaho' (U.S. Plant Pat. No. 6,679), (15.6%). Dry seed weight averages 3.28 mg/seed, and seeds are smaller than those of 'Marion' (non-patented) and 'Black Diamond' (non-patented) (each 3.95 mg seed).

Fruit clusters are medium-long (similar to 'Marion' (non-patented)), cymose, and are mostly borne on the periphery of the plant canopy, providing easy access to harvest. Flower fertility is high and clusters are well filled.

The new cultivar has been named the ONYX cultivar.

BRIEF DESCRIPTION OF THE PHOTOGRAPHS

Figure 2:
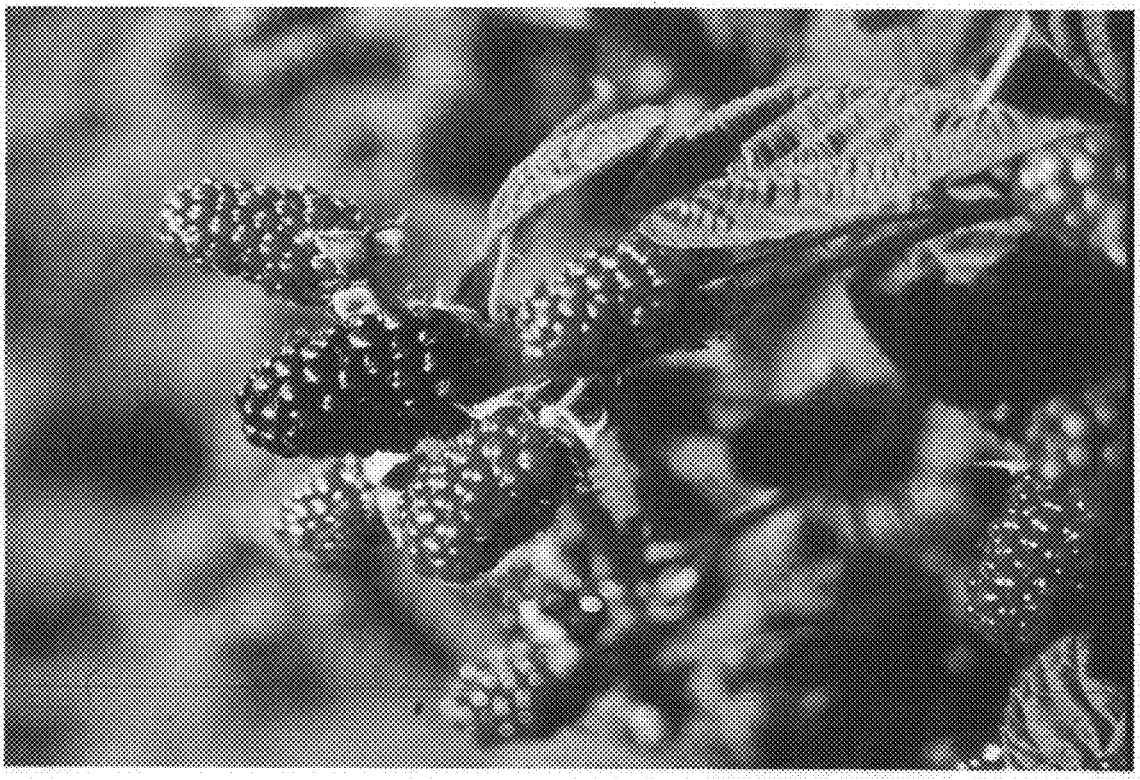
Figure 3:
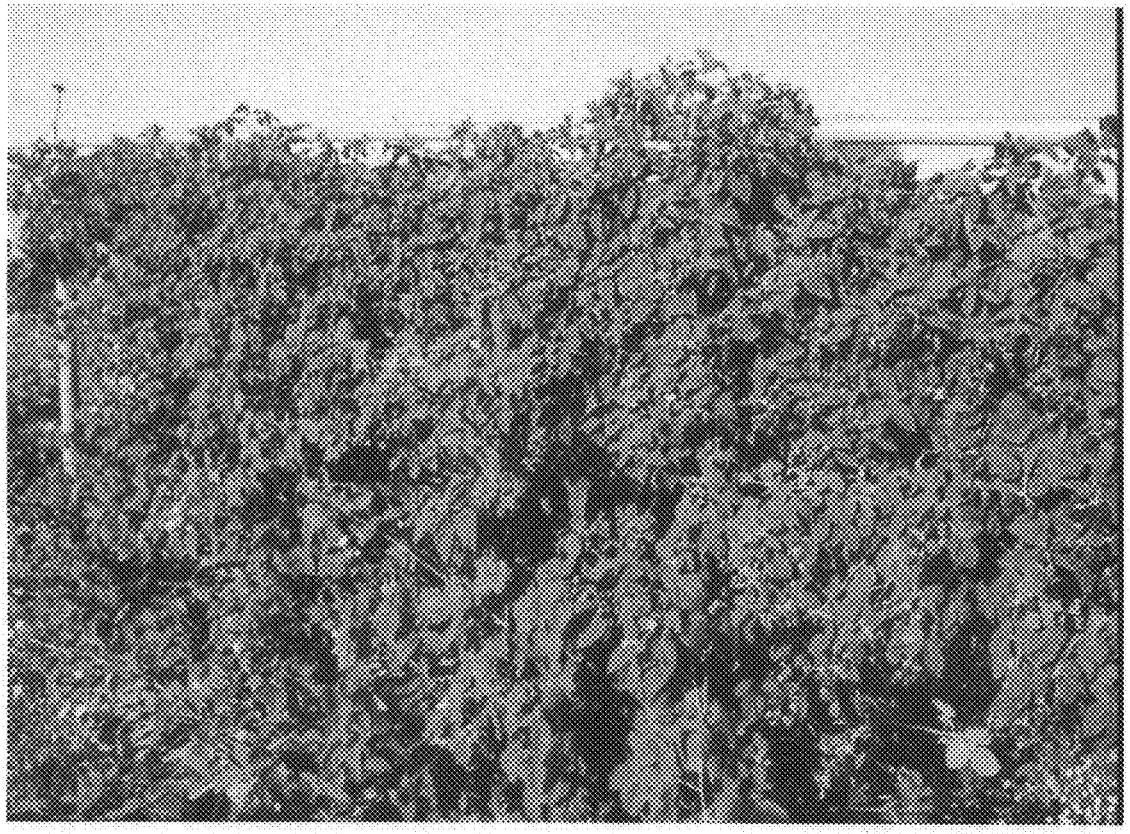

The accompanying photographs show typical specimens of the leaves and canes (FIG. 1); fruit and fruit cluster (FIG. 2), and entire five year old plant plant (FIG. 3) of the new variety in color as nearly true as it is reasonably possible to make in a color illustration of this character.

DETAILED DESCRIPTION OF THE NEW CULTIVAR

The following is a detailed description of the botanical and pomological characteristics of the subject blackberry. Color data are presented in Royal Horticultural Society Colour Chart (Fifth edition, 2007) designations.

Where dimensions, sizes, colors and other characteristics are given, it is to be understood that such characteristics are approximations of averages set forth as accurately as practicable.

The descriptions reported herein are from five year old specimens grown at Aurora or Corvallis, Oreg. with the measurements/observations for one trait always being made on samples from the same location. The plants used for these evaluations were planted in 2005.

Plant:

*Size.*—Medium cane length approximately 3.97 m; canes emerge radially from the plant crown and trail on the soil surface if not trained to a trellis as would be typical.

*Growth habit.*—Vigorous, with moderate suckering from crowns, canes are predominantly trailing but have more semi-erect canes than is typical for a western trailing blackberry like 'Marion' (non-patented).

*Growth rate.*—Primocanes reached 29 cm on 4/29, which was similar to 'Marion' (non-patented) (30.5 cm) but much taller than 'Black Diamond' (non-patented) (10.2 cm) on the same day.

*Productivity.*—High; ranged from 12.4 to 16.9 kg plant (5.65 to 7.7 lbs/plant) over 23 days (5-95% harvest). Yields are comparable to or higher than 'Marion' (non-patented) and lower than 'Black Diamond' (non-patented). The length of the harvest season is 23 days.

*Cold hardiness.*—Hardy to −12° C. (10° F.), comparable or better than 'Marion' (non-patented).

*Canes.*—Thorny, trailing. Cane diameter: base 0.93 cm, midpoint 0.69 cm. terminal 0.34 cm. Internode length: base 8.80 cm, midpoint 6.21 cm, terminal 6.87 cm. Thorn length base 4.42 mm, midpoint 5.23 mm, terminal 3.55 mm. Thorn density/30 cm: base 238, midpoint 164, terminal 95. Floricane color: base-Yellow-Green Group (152A); midpoint — Yellow-Green Group (146C); terminus — Yellow-Green Group (146C). Primocane color: base — Yellow-Green Group (144A) with streaking primarily Greyed-Orange Group (166A) and Greyed Purple Group (18313); midpoint — Yellow-Green Group (144B) stippled with Greyed-Purple Group (183B); terminus — Yellow-Green Group (146B). Date of primocane emergence: Day 91 after January 1 (April 1).

*Disease resistance.*—Moderate to anthracnose, septoria, septocyta, botrytis and yellow rust observed on plants in trial plots where these diseases were present on other genotypes.

Foliage:

*Primocane.*—Leaves — Medium. Mature compound leaf width 13.78 cm; length 12.63 cm. Terminal Leaflet: Width 6.38 cm; length 7.05 cm; Lateral leaflet : width 5.40 cm; length 7.12 cm; Terminal leaflet shape ovate to oval with acuminate/acute apex and round/cordate base; margin serrated, serration teeth length 0.19 cm, and width at base 0.17 cm; very light, coarse pubescence on adaxial surface and heavy soft pubescence on abaxial surface. Long prickles on sides and back of petioles, petiolules, midveins and lateral veins. Number of leaflets per compound leaf: usually 5 but ranges from 3-7. Color: abaxial — Yellow-Green Group (147A); adaxial — Yellow-Green Group (147B). Petioles — Length: 5.12 cm. Color: adaxial Yellow-Green Group (144A), abaxial Yellow-Green Group (144B). Petiolules — Length: terminal leaflet 2.62 cm, 1$^{st}$ distal leaflet 0.49 cm. Color: adaxial Yellow-Green Group (144B), abaxial Yellow-Green Group (144A). Stipules — Erect; Length: 1.42 cm. Width: 0.13 cm.

*Floricane.*—Leaves — Medium. Mature compound leaf width 9.43 cm; length 8.45 cm. Terminal Leaflet: width 4.38 cm; length 6.10 cm; Lateral leaflet: width 3.13 cm; length 4.77 cm; Terminal leaflet shape oval to ovate with acute apex and rounded to slightly cordate base; margin serrated, with serration teeth length 0.146 cm and width at base 0.219 cm; light pubescence on adaxial and medium on abaxial. Number of leaflets per compound leaf: 3. Color: abaxial-Yellow Green Group (147A); adaxial-Yellow Green Group (1478). Petioles — Length: 3.18 cm. Color: abaxial Yellow-Green Group (146B), adaxial Yellow-Green Group (146C). Petiolules — Length terminal leaflet 0.72 cm, 1st distal leaf 0.013. Color: abaxial Yellow-Green Group (146B); adaxial Yellow-Green Group (146C). Stipules — Length: 0.59 cm. Width: 0.07 cm.

Flowers:

*Date of bloom.*—First — Days from 1 January 145 (May 25); 50% — Days from 1 January 150 (May 30).

*Blossom color.*—White Group (NN155D).

*Reproductive organs.*—Stamens — erect, numerous: Pistils — numerous. Pollen — normal and abundant. Self fertile.

*Flower diameter.*—3.61 cm.

*Petal size.*—Length: 1.55 cm. Width: 1.17 cm.

*Number flowers per cluster.*—Mean of 6.3 with range of 5 to 8.

*Number of petals per flower.*—Mean 5.2.

*Number of sepals per flower.*—Mean 5.2.

*Cyme type.*—Elongate, simple cyme.

Fruit:

*Maturity.*—Late season, 7 days later than 'Marion' (non-patented). Mean 5% harvest date is July 9, Mean period of ripening (5%-95%) is July 9 to August 1.

*Size.*—Large, mean 6.1 g, uniform. Diameter: Fruit at primary position on inflorescence: equator 1.67 cm, base pole 2.43 cm, terminal pole 1.02 cm; fruit at secondary positions on inflorescence: equator 1.57 cm., base pole 1.50 cm, terminal pole 1.05 cm. Length (Primary fruit) 2.83 cm.

*Shape.*—Long, conical, uniform ratio length to width — 1.70.

*Color.*—Glossy black; Black Group (203C).

*Drupelet number per fruit.*—Medium, 83.

*Seed size.*—0.0033 g (dry wt., individual seed).

*Soluble solids.*—13.70% at 20° C.; compared to 'Marion' (non-patented) at 13.32%; (as measured on puree sample of fully-ripe berries).

*pH.*—3.64; compared to Marion at 3.32 (as measured on puree sample of fully-ripe berries).

*Titratable acidity.*—0.96 g citric acid/100 g fruit compared to 'Marion' (non-patented) at 1.36 g citric acid /100 g fruit (as measured on puree sample of fully-ripe berries).

*Processed quality.*—Excellent as individually quick frozen (IQF)I and puree.

*Uses.*—Primarily suited to fresh market but cane be processed readily into individually quick frozen fruit, puree, juice, or dried to make innumerable consumer products such as jellies, confections, and bakery items.

The variety: The most distinctive features of the variety are its high yields, large fruit size, excellent fresh fruit quality, especially firmness and flavor, mid-late season fruit ripening, and healthy trailing blackberry plants.

We claim:

1. A new and distinct variety of blackberry plant, substantially as illustrated and described, characterized by its high yields, large fruit size, excellent fresh fruit quality, mid-late season fruit ripening, and healthy plants.

* * * * *